(12) United States Patent
Echarri et al.

(10) Patent No.: US 9,669,188 B2
(45) Date of Patent: Jun. 6, 2017

(54) NONCIRCULAR INNER LUMEN GUIDING CATHETER WITH ASSISTED VARIABLE SUPPORT

(71) Applicant: DEPUY SYNTHES PRODUCTS, LLC, Raynham, MA (US)

(72) Inventors: Roberto Echarri, Miami, FL (US); Clifford D. Taylor, Pembroke Pines, FL (US); Eric Williams, Miramar, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 14/255,530

(22) Filed: Apr. 17, 2014

(65) Prior Publication Data

US 2014/0228749 A1 Aug. 14, 2014

Related U.S. Application Data

(62) Division of application No. 13/088,314, filed on Apr. 15, 2011, now Pat. No. 8,721,588.

(51) Int. Cl.
*A61M 25/00* (2006.01)
*A61B 17/12* (2006.01)
(Continued)

(52) U.S. Cl.
CPC ....... *A61M 25/005* (2013.01); *A61B 17/1214* (2013.01); *A61M 25/0026* (2013.01);
(Continued)

(58) Field of Classification Search
CPC .......... A61M 25/0026; A61M 25/0028; A61M 25/0029; A61M 25/003; A61M 25/0032;
(Continued)

(56) References Cited

U.S. PATENT DOCUMENTS 4,619,643 A 10/1986 Bai
4,998,917 A 3/1991 Gaiser
(Continued)

FOREIGN PATENT DOCUMENTS

CN 100400121 C 7/2008
EP 1121954 A1 * 8/2001
(Continued)

OTHER PUBLICATIONS

European Search Report, Sep. 12, 2012, 11 pages.
Japan Office Action JP2012-091688, dated Mar. 1, 2016.

*Primary Examiner* — Imani Hayman
*Assistant Examiner* — James Ponton

(57) ABSTRACT

A noncircular inner lumen guiding catheter with assisted variable support has an inner wall defining a noncircular cross-sectional shaped lumen for use in delivery of multiple microcatheters or other devices for treatment of neurovascular defects, such as for treatment of aneurysms. The noncircular inner lumen guiding catheter with assisted variable support includes torque transmittal guidance walls that are flexible linearly but not circumferentially, and that are neither collapsible nor kinkable. The noncircular shaped cross-section of the inner lumen may extend along the entire length of the catheter or a portion thereof, including distal or proximal.

16 Claims, 13 Drawing Sheets

(51) Int. Cl.
*A61M 25/06* (2006.01)
*A61M 25/02* (2006.01)

(52) U.S. Cl.
CPC .... *A61M 25/0032* (2013.01); *A61M 25/0043* (2013.01); *A61B 2017/1205* (2013.01); *A61M 25/0023* (2013.01); *A61M 25/0662* (2013.01); *A61M 2025/0059* (2013.01); *A61M 2025/0063* (2013.01); *A61M 2025/0293* (2013.01)

(58) Field of Classification Search
CPC .. A61M 2025/0035; A61M 2025/0037; A61M 25/005; A61M 25/0053; A61M 2025/0059; A61M 25/0063; A61M 25/0102; A61B 17/1214
See application file for complete search history.

(56) References Cited

U.S. PATENT DOCUMENTS

| | | | |
|---|---|---|---|
| 5,180,368 A | | 1/1993 | Garrison et al. |
| 5,195,962 A | * | 3/1993 | Martin et al. ............ 604/43 |
| 5,242,396 A | | 9/1993 | Evard |
| 5,487,757 A | | 1/1996 | Truckai et al. |
| 6,461,336 B1 | | 10/2002 | Larre |
| 6,562,021 B1 | | 5/2003 | Derbin et al. |
| 6,929,626 B2 | | 8/2005 | DiCarlo et al. |
| 7,182,755 B2 | | 2/2007 | Tal |
| 7,344,515 B2 | | 3/2008 | Coyle |
| 7,582,079 B2 | | 9/2009 | Wendlandt et al. |
| 7,766,049 B2 | | 8/2010 | Miller et al. |
| 7,879,004 B2 | | 2/2011 | Seibel et al. |
| 8,128,614 B2 | | 3/2012 | Abrams et al. |
| 2004/0002727 A1 | * | 1/2004 | Hwang et al. ............ 606/194 |
| 2005/0027287 A1 | | 2/2005 | O'Connor et al. |
| 2005/0065469 A1 | | 3/2005 | Tal |
| 2006/0270977 A1 | | 11/2006 | Fisher |
| 2007/0250039 A1 | * | 10/2007 | Lobbins et al. ............ 604/523 |
| 2008/0147000 A1 | | 6/2008 | Seibel |
| 2008/0243176 A1 | | 10/2008 | Weitzner et al. |
| 2009/0247868 A1 | | 10/2009 | Chesnin |

FOREIGN PATENT DOCUMENTS

| | | |
|---|---|---|
| JP | 8500253 A | 1/1996 |
| JP | 9-84878 A | 3/1997 |
| WO | 9613296 A1 | 5/1996 |
| WO | 9737716 A1 | 10/1997 |
| WO | 0176655 A2 | 10/2001 |
| WO | 03074107 A2 | 9/2003 |
| WO | 2005099802 A2 | 10/2005 |
| WO | 2006127929 A2 | 11/2006 |
| WO | 2007127176 A2 | 11/2007 |
| WO | 2009065552 A1 | 5/2009 |
| WO | 2009120871 A2 | 10/2009 |
| WO | WO 2010071816 A1 | 6/2010 |
| WO | WO 2010096579 A1 | 8/2010 |
| WO | 2011015434 A2 | 2/2011 |

* cited by examiner

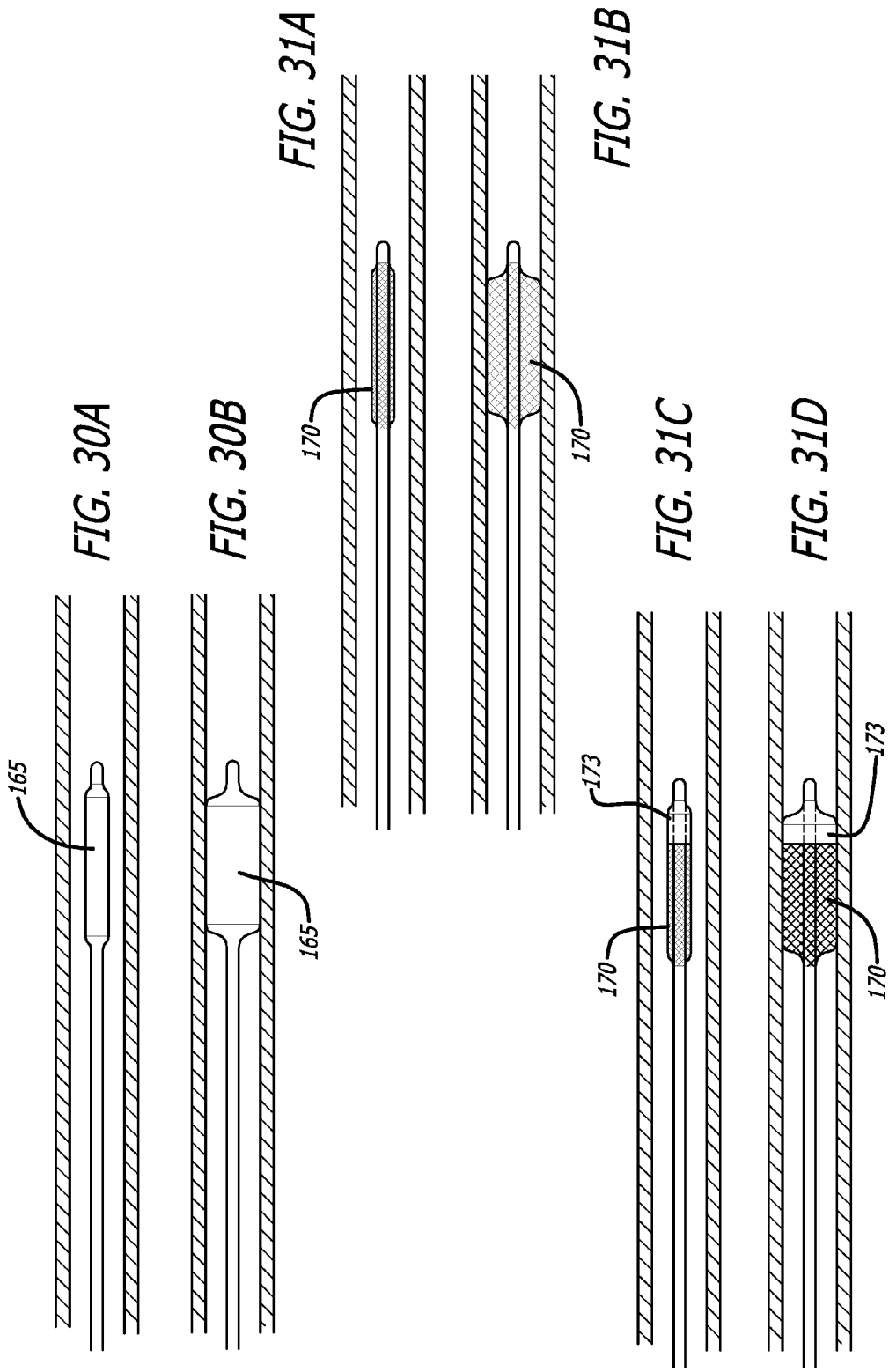

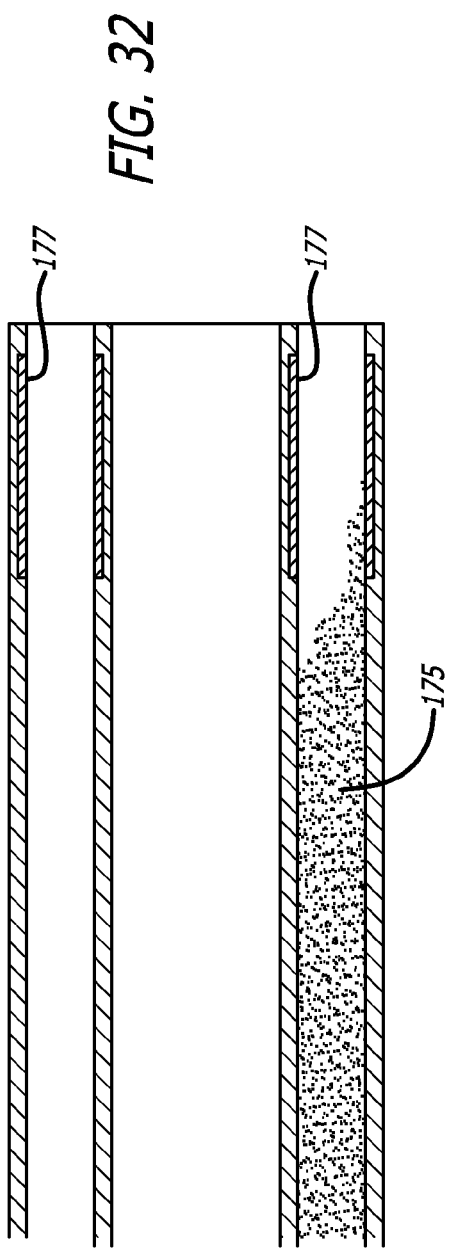
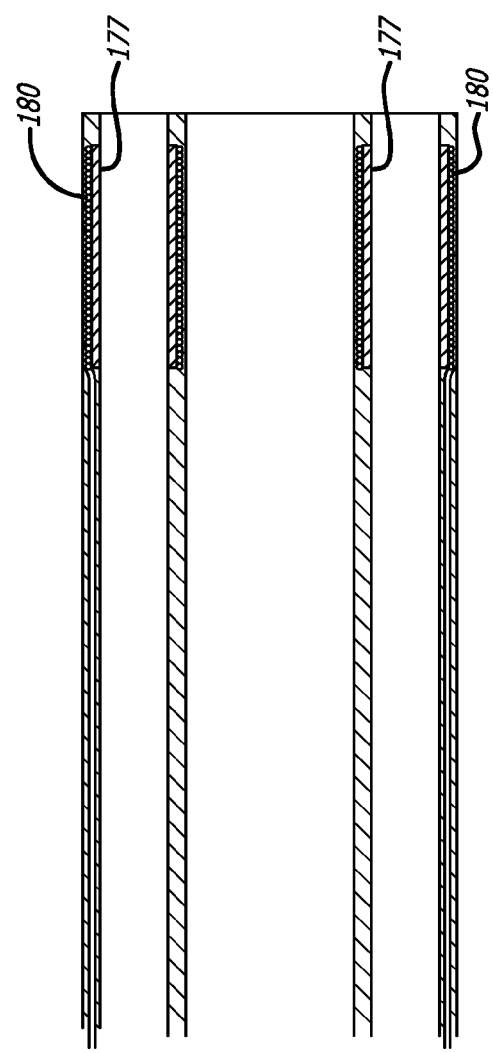

NONCIRCULAR INNER LUMEN GUIDING CATHETER WITH ASSISTED VARIABLE SUPPORT

CROSS-REFERENCES TO RELATED APPLICATION

This is a divisional of U.S. Ser. No. 13/088,314, filed on Apr. 15, 2011, which is hereby incorporated by reference as if set forth in full herein.

BACKGROUND OF THE INVENTION

The present invention relates generally to guiding catheters for the placement of devices for interventional therapeutic treatment of defects in the vasculature, and more particularly relates to guiding catheters having supplemental torque transmittal and guidance walls which may be designed to have variable linear flexibility compared to the rotational flexibility and torque-ability, and that are neither readily collapsible nor kinkable in use, for delivering intravascular interventional devices for treatment of defects in the neurovasculature, such as for treatment of aneurysms.

Vascular interventional devices such as vasoocclusive coils and the like may be typically placed within the vasculature by use of a catheter. Vasoocclusive devices may be either placed within a blood vessel to modify the flow of blood through the vessel by diverting or mitigating the flow of blood into a damaged or leaking portion of the vessel, or are placed within an aneurysm or other malformation stemming from the vessel to form an embolus within the aneurysm, or some combination of techniques to repair a neurovascular defect. Vasoocclusive devices used for these procedures can also have a wide variety of configurations, and aneurysms have been treated with external surgically placed clips, detachable vasoocclusive balloons and embolus generating vasoocclusive devices such as one or more vasoocclusive coils. The delivery of such vascular devices has ordinarily been accomplished by a variety of means, including via a catheter in which the device is pushed through an opening at the distal end of the catheter by a pusher to deploy the device. The vascular devices can be produced in such a way that they will pass through the lumen of a catheter in a linear shape and take on a complex shape as originally formed after being deployed into the area to be treated.

The insertion of a guiding catheter or delivery catheter system into a desired arterial site is the first step for modern forms of endovascular treatment, and one of the most important steps for treatment of defects in the neurovasculature. The size of the puncture site in an artery is critical, as is the ability to guide and torque the repair and treatment device to the desired location in the neurovasculature. Ordinarily, prior art guiding catheters have had a circular cross-sectional shape. It would be desirable to provide a guiding catheter or delivery catheter having a cross-sectional shape that will reduce the French size equivalent cross-section to reduce the size of the puncture site, while maintaining the advantages of a larger size catheter for delivery of a plurality of microcatheters to a treatment site. It would also be desirable to provide a guiding catheter or delivery catheter having a cross-sectional shape that can flex more easily and which can be constructed to have variable longitudinal and torque flex profiles. The present invention meets these and other needs.

SUMMARY OF THE INVENTION

Briefly, and in general terms, the present invention provides for a guiding catheter with at least one noncircular inner lumen with assisted variable support between the inner lumens and the outer surface of the catheter for use in delivery of multiple microcatheters to treat neurovascular defects. A noncircular inner lumen guiding catheter with assisted variable support of the present invention includes torque transmittal guidance structures in the area between the inner lumen that are designed to be relatively flexible along the longitudinal axis of the catheter, but are designed to be relatively resistant to torque and bending about the lateral axes of the catheter, thus enhancing the ability of the resulting catheter to resist local collapsing or kinking in use.

By changing the shape of the cross-section of a guiding catheter or delivery catheter having a lumen accommodating multiple microcatheters, the guiding catheter or delivery catheter can have a smaller cross-sectional area, and consequently a smaller puncture size. By changing the cross-sectional shape of the lumen of the catheter from a circle to a noncircular shape, two 0.017" devices can be accommodated in a 5 Fr equivalent guiding catheter that fits a 6 Fr introducer system, but has a smaller profile, thus limiting vessel trauma. The catheter shaft may be composed of a braid/coil construction that may also include a polymeric material, with a lubricious inner lumen of polytetrafluoroethylene (PTFE) available under the brand name Teflon® from E.I. Du Pont de Nemours and Company Corporation (Wilmington, Del.) to optimize the wire exchange process in the most distal sections of the arteries. The proximal area of the guiding catheter will have an ergonomically designed hub to allow a physician to easily manipulate the catheter, and to insert other medical devices. The guiding catheter includes a segmented, progressively compliant tip design configured to produce a linear change in stiffness over a longitudinal portion of the device, and incorporates a compliant polymeric material to minimize vessel trauma. The exterior of the catheter is covered with a polymer material to encapsulate a stainless steel and/or platinum braid/coil construction thereby protecting the walls of the arteries and other tissue. In a presently preferred embodiment, the polymer material may include a lubricious hydrophilic outer coating. In one presently preferred aspect, the guiding catheter has an inner lumen having a cross-section with a shape consisting of two parallel straight line segments connected at their extremities to two curved line segments. In another presently preferred aspect, the guiding catheter has an inner lumen having a cross-section with a flattened oval shape. In another presently preferred aspect, the guiding catheter has an inner lumen having a cross-section with a flattened circle shape. In another presently preferred aspect, the guiding catheter has an inner lumen with an oval cross-sectional shape throughout the entire device. In another presently preferred aspect, the guiding catheter can have a round outer cross-sectional shape along the length of the device, with a proximal portion having an inner lumen with a noncircular cross-sectional shape, and a distal portion having an inner lumen with a round cross-sectional shape.

In one of several aspects, the invention includes a guiding catheter, having elongated wall structure extending along a length of the catheter defining an inner lumen and an outer lumen, the inner lumen having a noncircular cross-sectional shape and the outer lumen substantially having the cross-sectional shape of at least a portion of a curved geometric figure.

In various embodiments, the outer wall of the outer lumen may vary in stiffness along its length. The guiding catheter may also have an elongated spring member disposed in an outer wall of the wall structure. The wall structure between the inner lumen and the outer lumen may include a torque guidance portion that is substantially flexible linearly and not circumferentially. The inner lumen may have a noncircular cross-sectional shape. The inner lumen may have a cross-sectional shape consisting of two straight parallel line segments connected to each other at each end by two curved line segments. The two curved line segments may be symmetric mirror images of each other. The inner lumen may have a cross-sectional shape of a flattened oval. The inner lumen may have a cross-sectional shape of a flattened circle. The inner lumen may substantially have the cross-sectional shape of a complete oval. The outer lumen may substantially have the cross-sectional shape of at least a portion of a curved geometric figure and may be disposed to one side of the inner lumen. The outer lumen may substantially have the cross-sectional shape of at least a portion of a circle and may be disposed to one side of the inner lumen. The wall structure may further define a second outer lumen having the cross-sectional shape of a portion of a circle disposed to another, opposite side of the inner lumen. The wall structure defining the inner lumen and the inner lumen may extend distally beyond the outer lumens. The catheter wall structure defining the lumens may include an outer catheter surface having a substantially circular shaped cross-section that tapers inwardly and distally to an outer catheter surface that continues distally having a noncircular shaped cross-section. For example, the noncircular shaped cross-section may consist of two straight parallel line segments connected to each other at each end by two curved line segments. The noncircular shaped cross-section may also be a flattened oval, a flattened circle, a figure of revolution representing substantially an oval, an oval, and the like. The wall structure defining the outer lumens may extend distally beyond the inner lumen. A distal portion of the wall structure may be segmented and progressively compliant. The guiding catheter may also have a free floating coil or spring constrained in an outer wall of the wall structure. The guiding catheter may also have an elongated stiffener in the outer lumen. The stiffener may vary in stiffness along its length. The elongated stiffener may taper along at least a portion of the length of the stiffener. The portion of the length of the elongated stiffener may have a continuously changing taper angle. The portion of the length of the elongated stiffener may have contiguous tapered segments having different taper angles.

In various embodiments of the present invention, one or more of the outer lumens may be expandable and/or collapsible. The guiding catheter may include a balloon that can be inflated to expand and/or deflated to collapse through the outer lumen(s) serving as inflation/deflation lumens to supply fluid to the balloon or to suction fluid out of the balloon. The balloon may be disposed on the outside of the catheter body or wall structure. The guiding catheter may include control wires within one or more of the outer lumens that can actuate a metal cage disposed on the outside of the catheter body or wall structure. A segment or a layer of the guiding catheter may be composed of a material that can be activated so that its state, form, or one or more properties or characteristics change. For example, the segment or layer may be heat-activated. A liquid injected into one or more of the outer lumens on the catheter body may activate this segment or layer of the guiding catheter. Or, an electric heating element inserted into one or more of the outer lumens may activate this segment or layer of the guiding catheter.

In another aspect, the invention includes a guiding catheter, having an elongated wall structure extending along a length of the catheter, defining an inner lumen and an outer lumen, the inner lumen having a noncircular cross-sectional shape and an elongated stiffener in the outer lumen. The noncircular cross-sectional shape may consist of two straight parallel line segments connected to each other at each end by two curved line segments. The two curved line segments may be symmetric mirror images of each other. Or, the noncircular cross-sectional shape may also be described as: substantially at least a portion of an oval, substantially at least a portion of a curved geometric figure, a flattened oval, a flattened circle, an oval, and the like.

In various embodiments, the stiffener may vary in stiffness along its length.

In yet another aspect, the invention includes a guiding catheter, having elongated wall structure extending along a length of the catheter defining an inner lumen and an outer lumen, the inner lumen having a noncircular cross-sectional shape and the wall structure varying in stiffness along the length. The noncircular cross-sectional shape may consist of two straight parallel line segments connected to each other at each end by two curved line segments. Or, the noncircular cross-sectional shape may also be described as: substantially at least a portion of an oval, substantially at least a portion of a curved geometric figure, a flattened oval, a flattened circle, an oval, and the like.

In various embodiments, the wall structure has segments of different materials. The guiding catheter may also have an elongated spring member disposed in an outer wall of the wall structure.

In a further aspect, the invention includes a guiding catheter, having elongated wall structure extending along a length of the catheter defining an inner lumen and an outer lumen, the inner lumen having a noncircular cross-sectional shape and the elongated wall structure including an outside wall having a surface with a shape that changes along the length between a circular and a noncircular cross-sectional shape. The noncircular cross-sectional shape of the inner lumen and the noncircular cross-sectional shape of a portion of the surface of the outside wall of the elongated wall structure may consist of two straight parallel line segments connected to each other at each end by two curved line segments. The two curved line segments may be symmetric mirror images of each other. Or, the noncircular cross-sectional shape may also be described as: substantially at least a portion of an oval, substantially at least a portion of a curved geometric figure, a flattened oval, a flattened circle, an oval, and the like.

In various embodiments, the guiding catheter may also have an elongated spring member disposed in an outer wall of the wall structure.

These and other aspects and advantages of the invention will become apparent from the following detailed description and the accompanying drawings, which illustrate by way of example the features of the invention.

BRIEF DESCRIPTION OF THE DRAWINGS

FIG. 30A-B are schematic diagrams of the catheter in a blood vessel showing the outer lumen as an inflation/deflation lumen for a balloon disposed on an outside of the catheter body in collapsed and expanded configurations.

FIG. 31A-D are schematic diagrams of the catheter in a blood vessel showing the expandable/collapsible metal cage disposed on an outside of the catheter body and actuated through control wires in the outer lumens in collapsed and expanded configurations with and without a distal membrane.

FIG. 32 is a schematic diagram of a liquid injected into the outer lumen in order to activate a layer or a segment of the wall structure of the guiding catheter body.

FIG. 33 is a schematic diagram of an electric heating element inserted into the outer lumen in order to activate a layer or a segment of the wall structure of the guiding catheter body.

DETAILED DESCRIPTION OF THE PREFERRED EMBODIMENTS

Figures 1, 2:
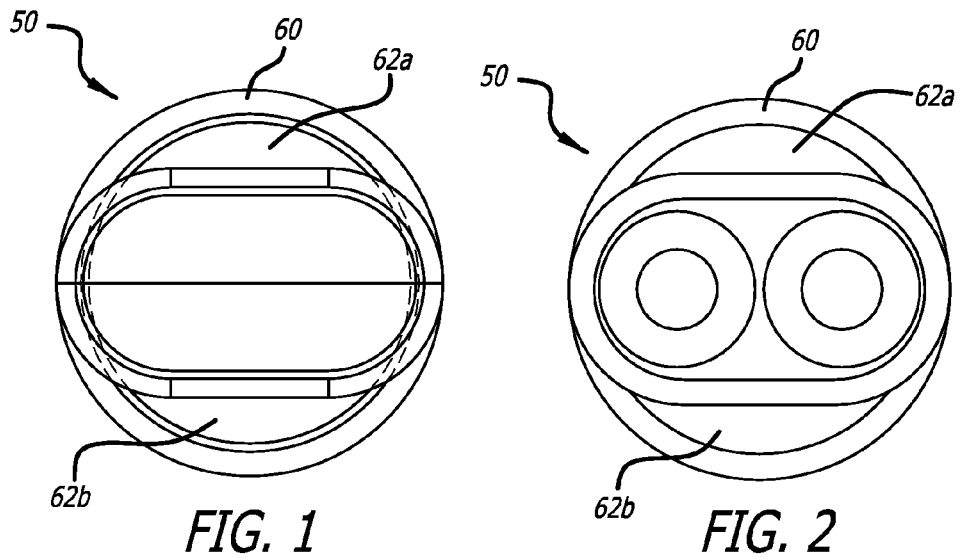
FIG. 1 is a front view of a schematic cross-sectional diagram of a first embodiment, illustrating a guiding catheter having a noncircular inner lumen and a round outer surface, showing the gaps or outer lumens between the noncircular inner walls and the round outer walls of the guiding catheter.
FIG. 2 is a front view of a schematic cross-sectional diagram of the guiding catheter of FIG. 1, with two microcatheters within the noncircular inner lumen.

Referring to the drawings, which are provided by way of example, and not by way of limitation, the present invention generally provides for a noncircular inner lumen guiding catheter.

Figure 3:
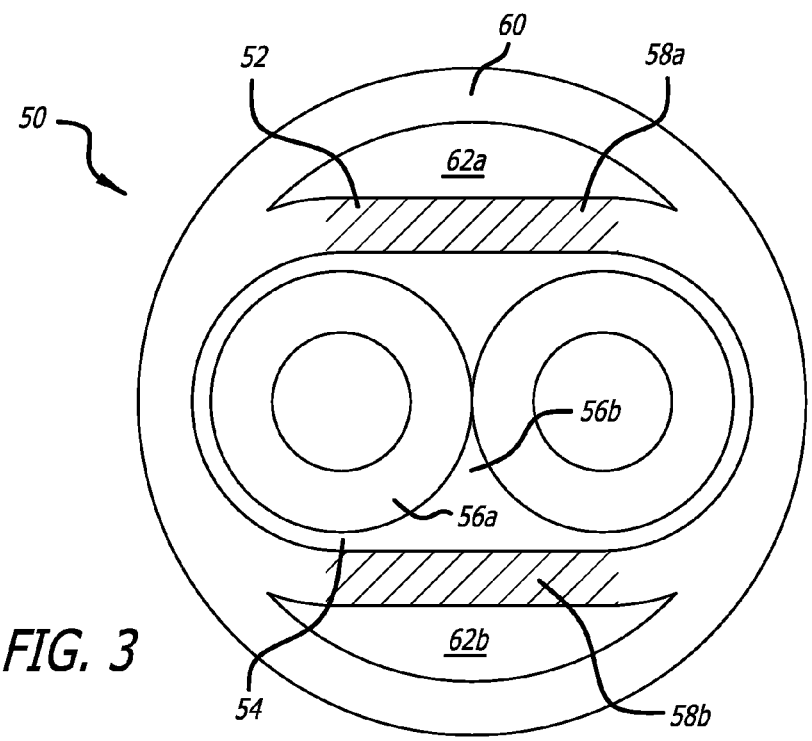
FIG. 3 is a front view of a schematic cross-sectional diagram illustrating elements and exemplary dimensions of the guiding catheter (with two microcatheters) of FIG. 2.
Figure 4:
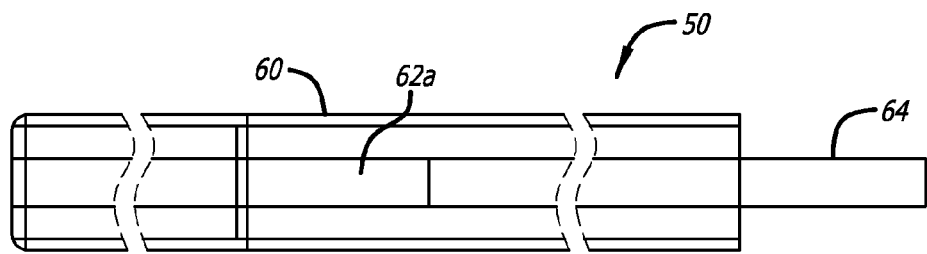
FIG. 4 is a top view of a schematic diagram of the guiding catheter of FIG. 1 illustrating insertion of stiffening devices in the gaps or outer lumens between the noncircular inner walls and the round outer walls of the guiding catheter.
Figure 5:
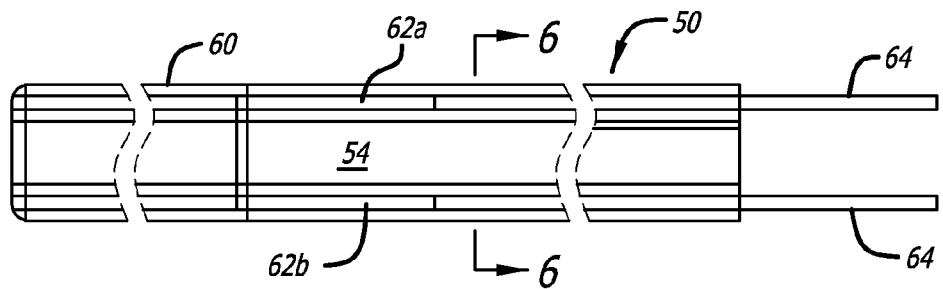
FIG. 5 is a side view of a schematic diagram of the guiding catheter of FIG. 4.
Figure 6:
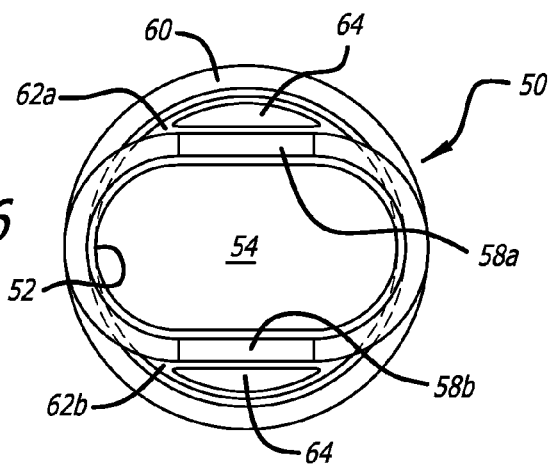
FIG. 6 is a schematic cross-sectional diagram of the guiding catheter taken along line 6-6 of FIG. 5.
Figure 7:
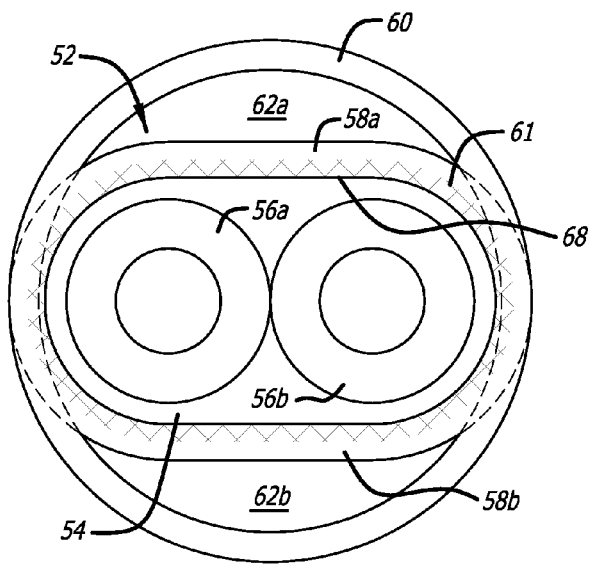
FIG. 7 is a further detailed schematic cross-sectional diagram illustrating elements of the guiding catheter (with two microcatheters) of FIG. 2.
Figure 8:
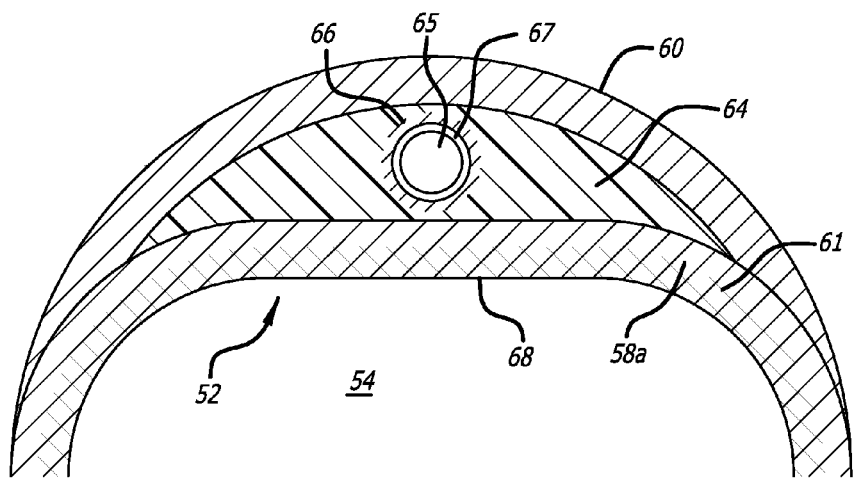
FIG. 8 is an enlarged sectional view similar to FIG. 7 illustrating additional elements for the guiding catheter of FIG. 1.
Figure 9:
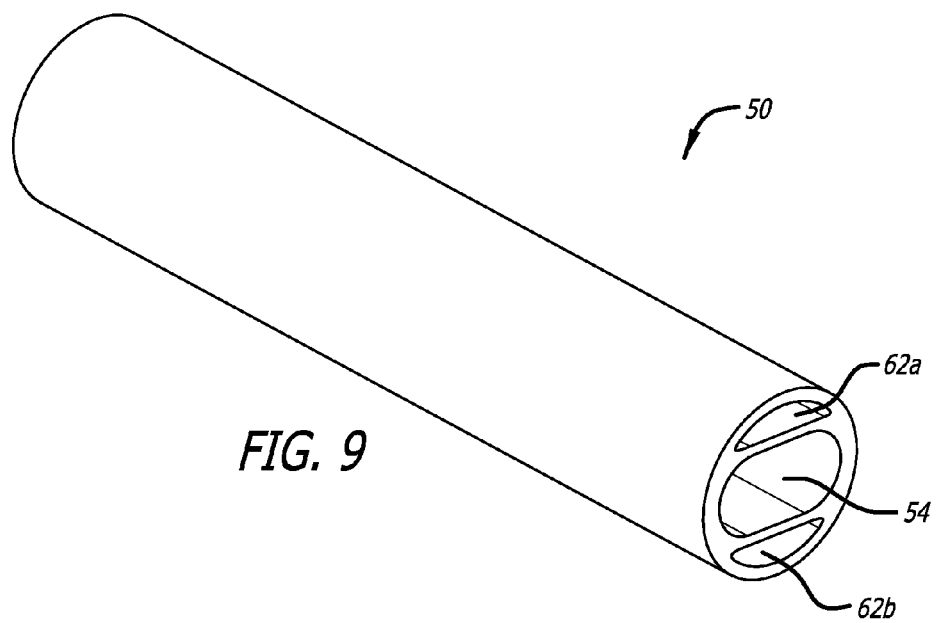
FIG. 9 is an isometric view of the guiding catheter of FIG. 1.
Figure 10:
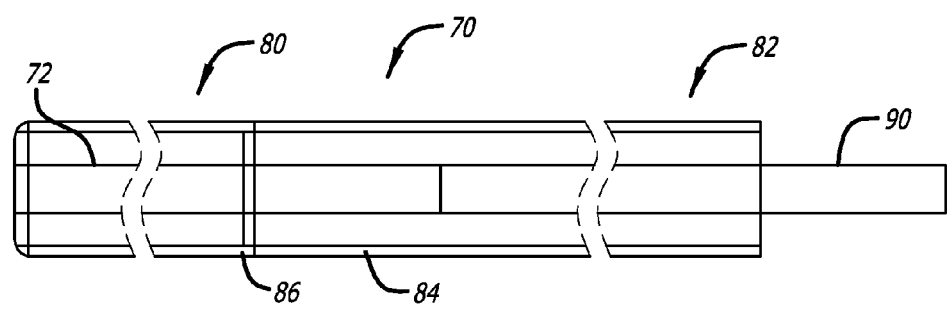
FIG. 10 is a top view of a schematic diagram of a second embodiment of a guiding catheter with a noncircular inner lumen, and a round outer surface that does not extend the full length of the device.
Figure 11:
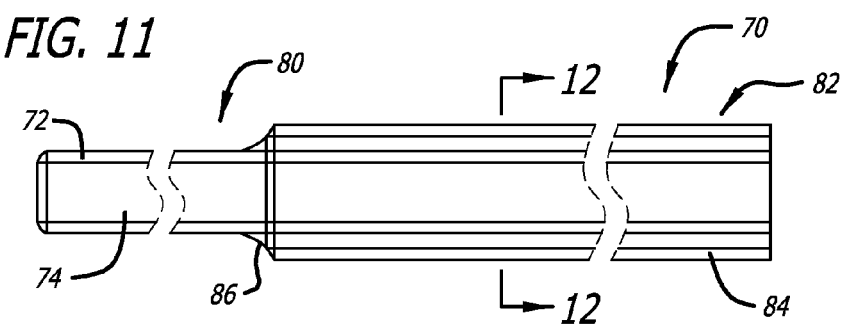
FIG. 11 is a side view of a schematic diagram of the guiding catheter according to the second embodiment.
Figure 12:
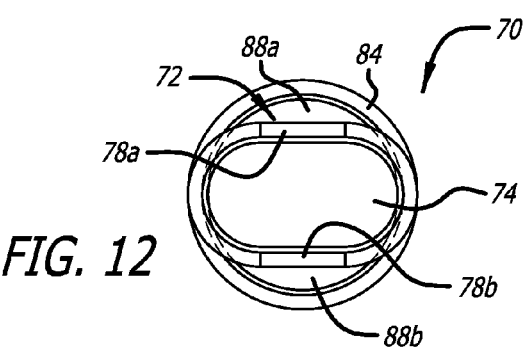
FIG. 12 is a schematic cross-sectional diagram of the guiding catheter taken along line 12-12 of FIG. 11.
Figure 13:
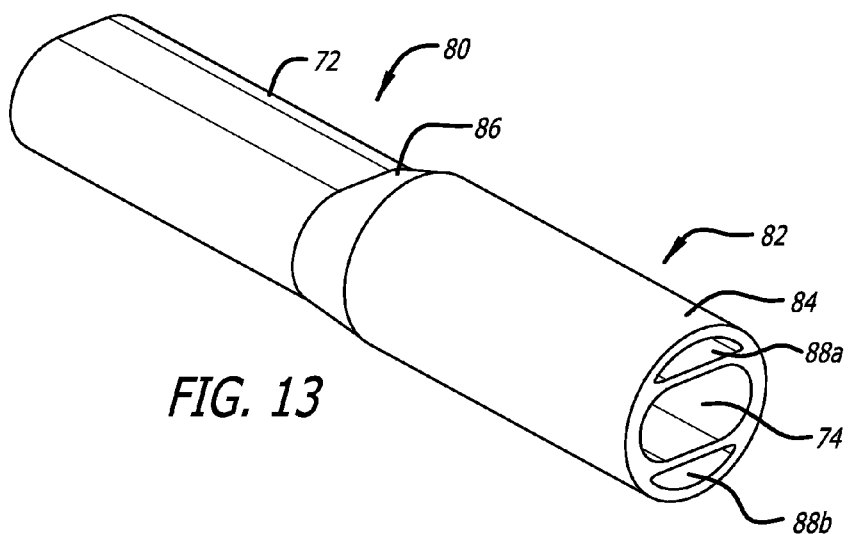
FIG. 13 is an isometric view of the guiding catheter according to the second embodiment.
Figure 14:
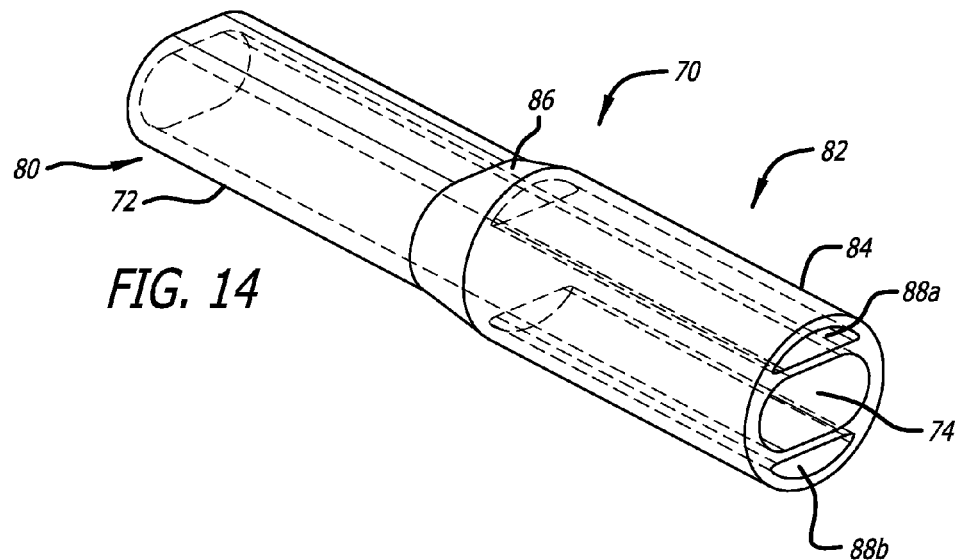
FIG. 14 is an isometric view of a schematic diagram of the guiding catheter according to the second embodiment.
Figure 15:
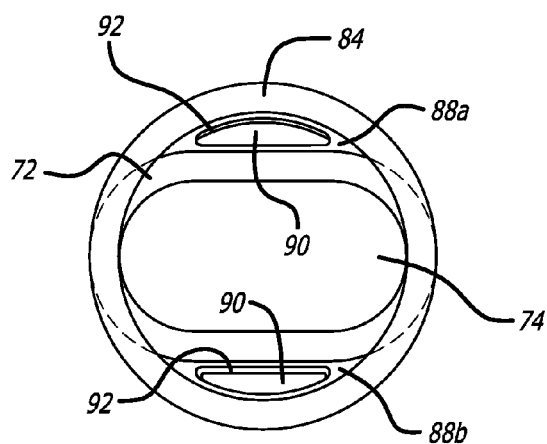
FIG. 15 is a schematic cross-sectional view of the guiding catheter of FIG. 10 similar to FIG. 12 including stiffening devices filling the gaps or outer lumens between the noncircular inner walls and the round outer walls of the guiding catheter.
Figure 16:
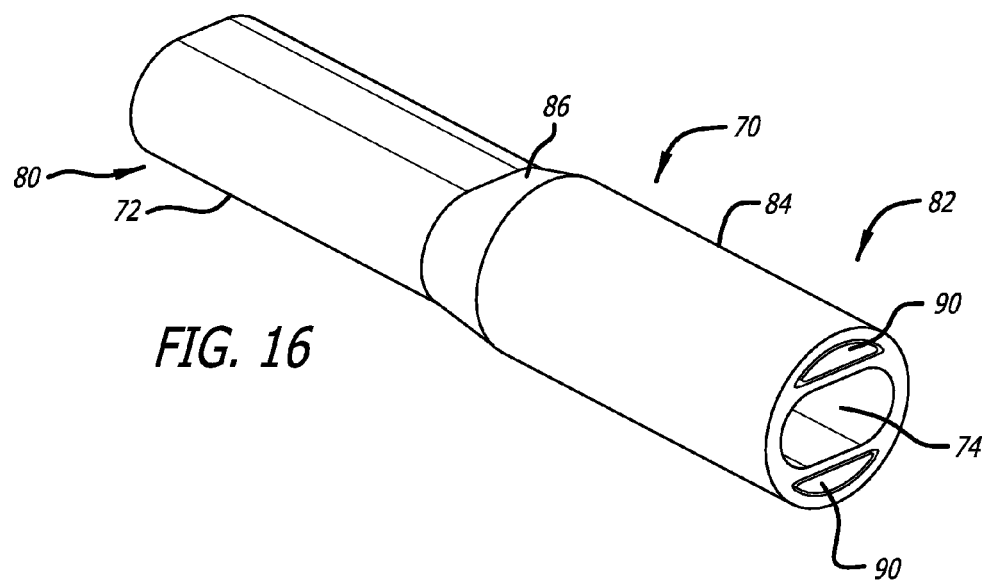
FIG. 16 is an isometric view of the guiding catheter of FIG. 15.
Figure 17:
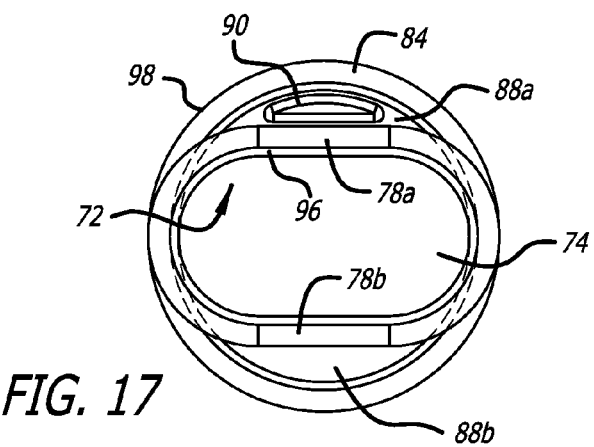
FIG. 17 is a schematic cross-sectional view of the guiding catheter of FIG. 10 similar to FIG. 12 including one stiffening device filling one of the gaps or outer lumens between the noncircular inner walls and the round outer walls of the guiding catheter.
Figure 18:
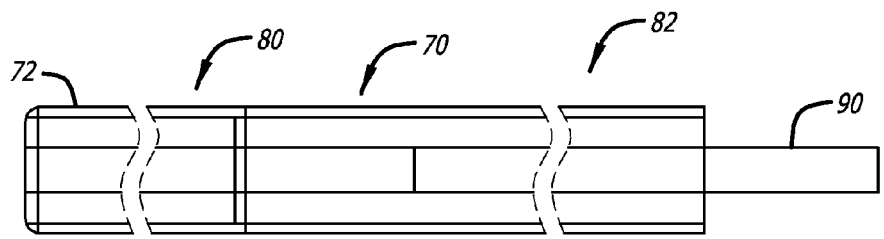
FIG. 18 is a top view of a schematic diagram similar to FIG. 10 illustrating insertion of stiffening devices in the gaps or outer lumens between the noncircular inner walls and the round outer walls of the guiding catheter.
Figure 19:
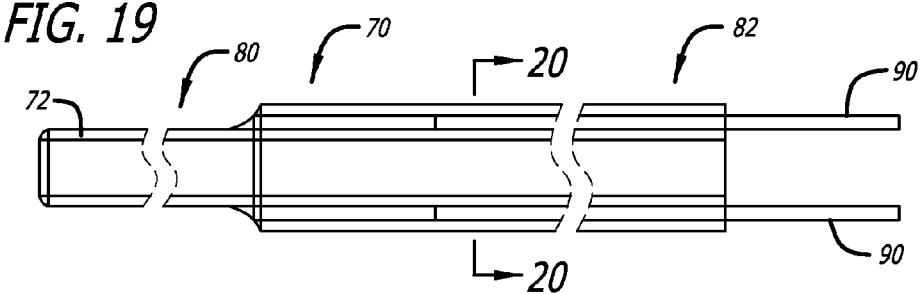
FIG. 19 is a side view of a schematic diagram of the guiding catheter of FIG. 18.
Figure 20:
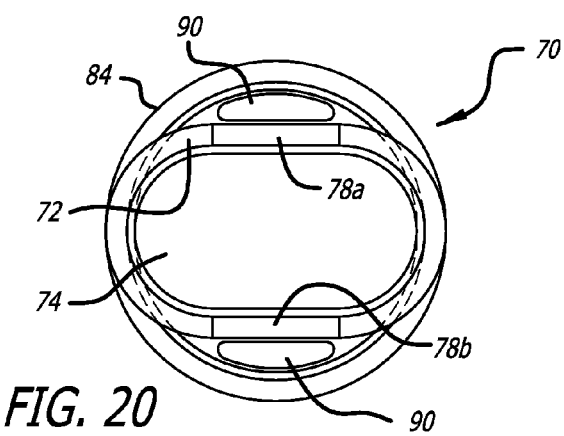
FIG. 20 is a schematic cross-sectional view of the guiding catheter taken along line 20-20 of FIG. 19.
Figure 21:
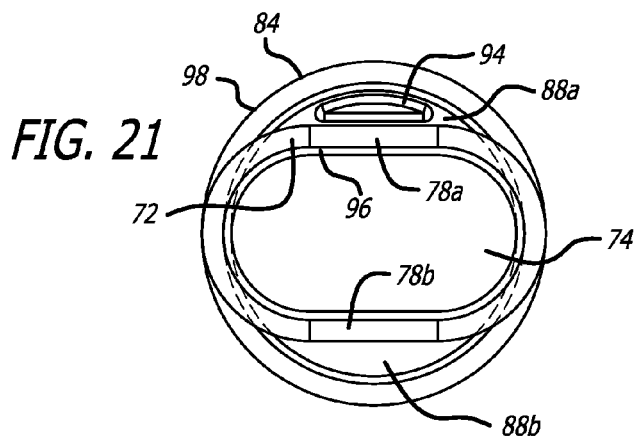
FIG. 21 is a schematic cross-sectional view of the guiding catheter of FIG. 10 similar to FIG. 12 including one hypotube stiffening device filling one of the gaps or outer lumens between the noncircular inner walls and the round outer walls of the guiding catheter.
Figure 29:
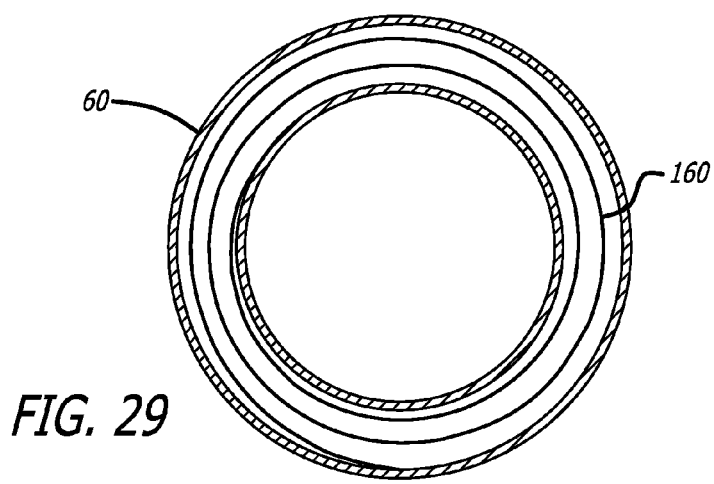
FIG. 29 is a schematic cross-sectional diagram of the guiding catheter in which the external wall has a coil or spring in it, in accordance with an embodiment of the present invention.

Referring to FIGS. 1-9, in a first presently preferred embodiment, the present invention provides for a noncircular inner lumen guiding catheter with assisted variable support 50 having a noncircular inner lumen wall 52 defining an inner lumen 54 having a noncircular cross-sectional shape for use in delivery of multiple microcatheters 56a, 56b for treatment of neurovascular defects, such as for treatment of aneurysms. The noncircular inner lumen guiding catheter with assisted variable support of the present invention includes torque transmittal guidance walls 58a, 58b that are flexible linearly but not circumferentially, and that are neither collapsible nor kinkable. For example, this may be accomplished, in whole or in part, by the torque transmittal guidance walls being made of a different material than the remainder of the guiding catheter wall structure as shown in FIG. 3. More specifically, according to an embodiment, the torque transmittal guidance walls may flex in a dimension perpendicular to a flat cross-sectional surface of the walls but may not flex in a dimension parallel to a flat cross-sectional surface of the walls. The outer surface can have a round outer wall 60 with a round cross-sectional shape, which typically extends from the proximal end or hub of the device to the distal end or tip, while the inner lumen remains noncircular. As is illustrated in FIGS. 7 and 8, the inner lumen can be reinforced by a coil or braid 61, and the braid can have a variable braid angle. The noncircular inner lumen guiding catheter preferably also includes first and second gaps or outer lumens 62a, 62b, defined between the noncircular inner wall and the round outer wall of the guiding catheter (see FIGS. 3-5, 7, and 9). The round outer surface of the device may be composed of polymeric material segments progressively compliant that are configured to produce a linear change in stiffness over a longitudinal desired portion of the device. The external layer also can be built in such a way that it has a free floating coil or spring 160 (FIG. 29) constrained in it. One end of this coil or spring may be affixed to the noncircular inner surface, while the other end is affixed to a push/pull mechanism that rides along the gaps or outer lumens between the noncircular inner surface and the outer surface 69. Actuation of the mechanism will compress or extend the coil or spring. This action will stiffen or loosen/soften the catheter shaft.

Figure 25:
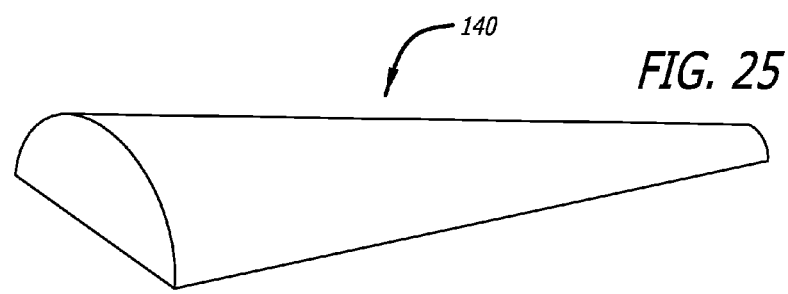
FIG. 25 is a side view of a stiffening device that tapers along its length in accordance with the present invention.
Figure 26:
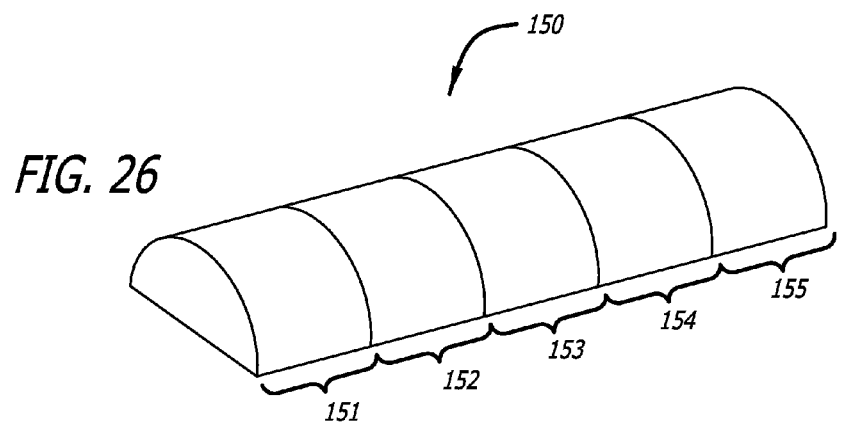
FIG. 26 is a side view of a stiffening device comprised of different materials along its length in accordance with the present invention.
Figure 27:
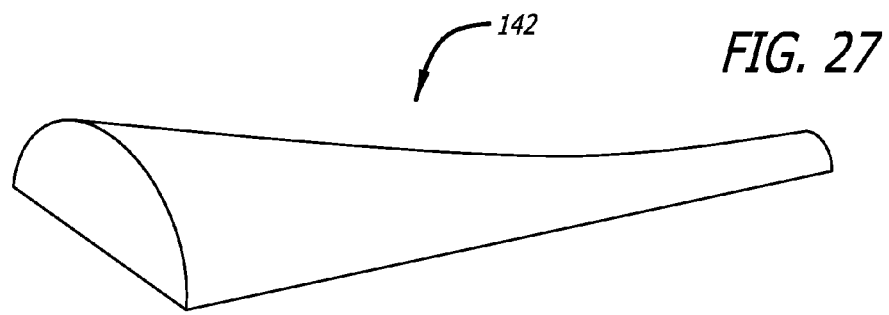
FIG. 27 is a side view of a stiffening device with a continuously changing taper angle in accordance with the present invention.
Figure 28:
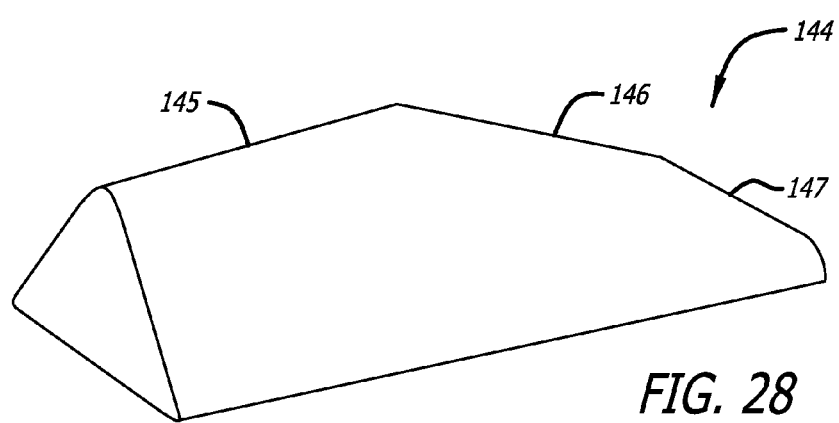
FIG. 28 is a side view of a stiffening device having contiguous tapered segments with different taper angles.

As is illustrated in FIGS. 4-6 and 8, the gaps or outer lumens between the noncircular inner wall and the round outer wall of the guiding catheter may be used as separate lumens for insertion or manipulation of one or more stiffening devices 64 that can help prevent the catheter from backing out of certain positions once inside the circulatory system. These stiffening devices may be composed of a round metal wire, a flat wire, a hypotube not conforming to the shape of the gap, a wire with the shape of the gap, or a hypotube with the shape of the gap. The stiffening devices may be made out of different materials (not limited to metals) and may change material along their length. For example, as shown in FIG. 26, according to an embodiment of the invention, a stiffening device 150 may have various sections 151, 152, 153, 154, 155 formed of different materials. According to one embodiment shown in FIG. 25, the stiffening device may be a tapered stiffening device 140 that changes thickness or tapers along its length. As shown in FIG. 27, according to one embodiment, the stiffening devices may have a section 142 with a continuously changing taper angle to produce a curvilinear profile that is configured to produce a linear change in stiffness of the catheter. As shown in FIG. 28, according to one embodiment, the stiffening devices may have a section 144 of contiguous tapered segments 145, 146, 147 having taper angles that are configured to produce a linear change in stiffness over a longitudinal portion of the device. The stiffening devices may have a lubricious coating. As is illustrated in FIG. 8, one form of a stiffening device can be formed of a polymeric material conforming to the shape of a gap, including a central wire 65, which can include an outer reinforcement 66 formed of a coil or braid, and can include a PTFE coating 67. The stiffening devices are preferably secured to the outside of the noncircular inner surface of the gap, but are free to move throughout the length of the device. A simple action by the user on the proximal end will actuate them in such a way that one of them will be pushed while the other one will be pulled simultaneously provoking an increase in the overall stiffness of the proximal end of the catheter. The gaps or outer lumens also may be used as separate lumens for insertion of push/pull mechanism elements to make the tip of the catheter deflectable.

The catheter shaft preferably is composed of a stainless and/or platinum braid/coil construction, with a lubricious inner lumen coating 68 of PTFE to optimize the wire exchange process in the most distal sections of the arteries. The proximal area (not shown) will have an ergonomically designed hub to allow the physician to easily manipulate the catheter as well the insertion of other medical devices.

Referring to FIGS. 10-21, in a second presently preferred embodiment, the present invention provides for a noncircular inner lumen guiding catheter with assisted variable support 70 having a noncircular inner lumen wall 72 defining an inner lumen 74 having a noncircular cross-sectional shape for use in delivery of multiple microcatheters for treatment of neurovascular defects, such as for treatment of aneurysms. The noncircular inner lumen guiding catheter with assisted variable support of the present invention includes torque transmittal guidance walls 78a, 78b that are flexible linearly but not circumferentially, and that are neither collapsible nor kinkable.

Referring to FIGS. 10-14, the noncircular inner lumen guiding catheter includes a distal portion 80, and a proximal portion 82 also including a round outer wall 84 extending only a portion of the length of the guiding catheter, and an outer tapered transition wall 86 transitioning from the noncircular outer shape of the distal portion and the round outer shape of the proximal portion. The round outer surface typically stops somewhere along the length of the catheter, making a transition from a round proximal section to a noncircular distal section, with a noncircular lumen extending throughout the catheter. Thus, the noncircular lumen/wall may make up the only lumen/wall in the distal portion and the inner lumen/wall in the proximal portion. This feature helps with the stability of the proximal end of the device and yet having a distal section with smaller profile than conventional guiding catheters resulting in less trauma. First and second gaps or outer lumens 88a, 88b are defined between the noncircular inner wall and the proximal round outer wall of the guiding catheter as shown in FIGS. 12-15, 17, and 21.

As is illustrated in FIGS. 15-21, the gaps or outer lumens 88a, 88b between the noncircular inner wall and the round outer wall of the guiding catheter may be used as separate lumens for insertion or manipulation of one or more stiffening devices 90 that can help prevent the catheter from backing out of certain positions once inside the circulatory system. These stiffening devices may be composed of a round metal wire, a flat wire, a hypotube not conforming to the shape of the gap, a solid wire 92 with the shape of the gap, or a hypotube 94 with the shape of the gap. The stiffening devices may be made out of different materials (not limited to metals). The stiffening devices may have a section with a continuously changing taper angle to produce a curvilinear profile that is configured to produce a linear change in stiffness of the catheter. The stiffening devices may have a section of contiguous tapered segments having taper angles that are configured to produce a linear change in stiffness over a longitudinal portion of the device. The stiffening devices may have a lubricious coating. The stiffening devices are preferably secured to the outside of the noncircular inner surface of the gap, but are free to move throughout the length of the device. A simple action by the user on the proximal end may actuate them in such a way that one of them will be pushed while the other one will be pulled simultaneously provoking an increase in the overall stiffness of the proximal end of the catheter. The gaps or outer lumens also may be used as separate lumen(s) for insertion of push/pull mechanism elements to make the tip of the catheter deflectable.

The catheter shaft preferably is composed of a stainless and/or platinum braid/coil construction, with a lubricious inner lumen coating 96 of PTFE to optimize the wire exchange process in the most distal sections of the arteries. The proximal area (not shown) will have an ergonomically designed hub to allow the physician to easily manipulate the catheter as well as to insert other medical devices. The exterior of the catheter is preferably covered with a polymer material 98 to encapsulate the stainless and/or platinum braid/coil construction. The polymer material preferably has a lubricious hydrophilic outer coating.

Figure 22:
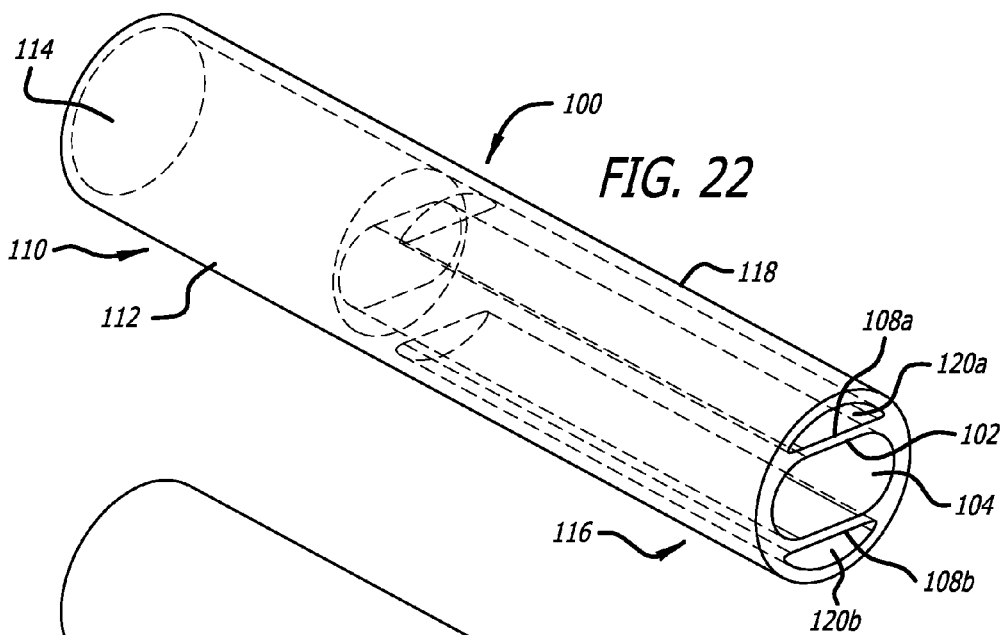
FIG. 22 is an isometric view of a schematic diagram of a third embodiment of a guiding catheter having a round outer shape along the length of the device, with a proximal portion having an inner lumen with a noncircular shape, and a distal portion having an inner lumen with a round shape.
Figure 23:
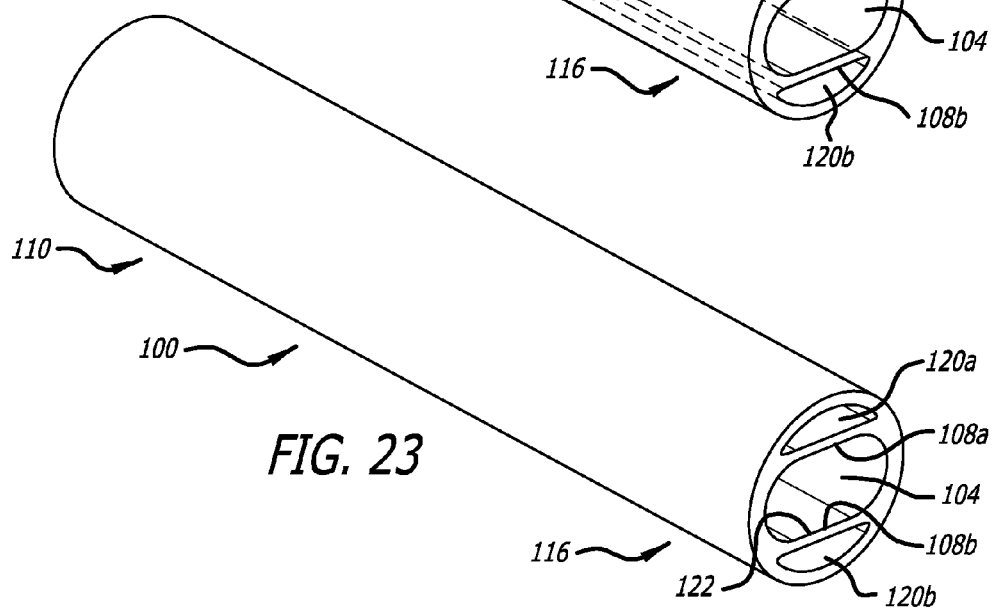
FIG. 23 is an isometric view of the guiding catheter of FIG. 22.

Referring to FIGS. 22-23, in a third presently preferred embodiment, the present invention provides for a noncircular inner lumen guiding catheter with assisted variable support 100 having a noncircular inner lumen wall 102 defining an inner lumen 104 having a noncircular cross-sectional shape for use in delivery of multiple microcatheters (not shown) for treatment of neurovascular defects, such as for treatment of aneurysms. The noncircular inner lumen guiding catheter with assisted variable support of the present invention includes torque transmittal guidance walls 108a, 108b that are flexible linearly but not circumferentially, and that are neither collapsible nor kinkable. The entire catheter outer surface is round and the lumen changes from noncircular on the proximal end to a very flexible round on the distal end. Referring to FIG. 22, the noncircular inner lumen guiding catheter includes a distal portion 110 with a round outer wall 112 defining a round inner lumen 114, and a proximal portion 116 also including a round outer wall 118 contiguous with the distal round outer wall. First and second gaps or outer lumens 120a, 120b are defined between the noncircular inner wall and the proximal round outer wall of the guiding catheter as shown in FIG. 22-23. The device is reinforced with braid/coil and different polymer segments.

The gaps or outer lumens between the noncircular inner wall and the round outer wall of the guiding catheter may be used as separate lumens for insertion or manipulation of one or more stiffening devices (see stiffening device 64 in FIGS. 4-6, central wire 65 in FIG. 8, stiffening device 90 in FIGS. 10, 15-20, hypotube 94 in FIG. 21, tapered stiffening device 140 in FIG. 25, stiffening device 150 in FIG. 26, tapered stiffening device 142 in FIG. 27, and section of tapered segments 144 in FIG. 28) that can help prevent the catheter from backing out of certain positions once inside the circulatory system. These stiffening devices may be composed of a round metal wire, a flat wire, a hypotube not conforming to the shape of the gap, a wire with the shape of the gap, or a hypotube with the shape of the gap. The stiffening devices may be made out of different materials (not limited to metals). The stiffening devices may have a section with a continuously changing taper angle to produce a curvilinear profile that is configured to produce a linear change in stiffness of the catheter. The stiffening devices may have a section of contiguous tapered segments having taper angles that are configured to produce a linear change in stiffness over a longitudinal portion of the device. The stiffening devices may have a lubricious coating. The stiffening devices are preferably secured to the outside of the noncircular inner surface of the gap, but are free to move throughout the length of the device. A simple action by the user on the proximal end will actuate them in such a way that one of them will be pushed while the other one will be pulled simultaneously provoking an increase in the overall stiffness of the proximal end of the catheter. The gaps or outer lumens also may be used as separate lumen(s) for insertion of push/pull mechanism to make the tip of the catheter deflectable.

The catheter shaft preferably is composed of a stainless and/or platinum braid/coil construction, with a lubricious inner lumen coating 122 of PTFE to optimize the wire exchange process in the most distal sections of the arteries. The proximal area will have an ergonomically designed hub to allow the physician to easily manipulate the catheter as well the insertion of other medical devices.

Referring to FIGS. 30A and 30B, the outer lumens formed between the noncircular inner lumen and the round outer surface of the catheter may serve as inflation/deflation lumens for a polymer balloon 165. The polymer balloon may provide catheter proximal support or flow arrest during an interventional therapeutic procedure. The balloon may be restricted to a proximal portion of the shaft to provide catheter proximal support or it may extend along a length or the entire length of the shaft. By supplying fluid to or suctioning fluid out of the outer inflation/deflation lumens the balloon may be reversibly collapsed and expanded repetitively as needed. The balloon may be anchored in place to provide and maintain flow arrest. The balloon may be disposed on the outside of the catheter body or wall structure and communicates with outer inflation/deflation lumens that supply/suction fluid to the balloon through an opening in the outer catheter body or wall structure.

Referring to FIGS. 31A and 31B, the outer lumens between the noncircular inner lumen and the round outer surface of the catheter running along the substantially flat torque transmittal guidance walls may be used to run control wires to actuate a metal cage 170. A version or a portion of the metal cage may be used for device support at various desired positions along the length of the guiding catheter. For example, a metal cage expanded through actuation of control wires within the outer lumens at the proximal end of the catheter may provide proximal support to the catheter. In another version of the metal cage or in a restricted portion of the metal cage a polymeric membrane 173 may be provided. The polymeric membrane may take the form of a silicone coating, for example. A polymeric membrane on the distal end of the metal cage may be used for flow arrest. The metal cage may be reversibly collapsed and expanded repetitively as needed, through actuation of control wires disposed in the outer lumens. The metal cage may be actuated by control wires contained in the two small outer lumens in round jacketing.

Referring to FIG. 32, in another application for the outer lumens or gaps alongside the torque transmittal guidance walls between the noncircular inner lumen and the round outer surface, the outer lumens may be used for injection of a liquid 175 therein. Injection of a liquid at a certain temperature into the outer lumens may serve to activate a desired polymer segment or polymer layer 177 on the catheter body.

Referring to FIG. 33, in still another application for the outer lumens they may be used for insertion of an electric heating element 180. Insertion of an electric heating element at a certain temperature into the outer lumens may serve to activate a desired polymer segment or polymer layer 177 on the catheter body.

Figure 24:
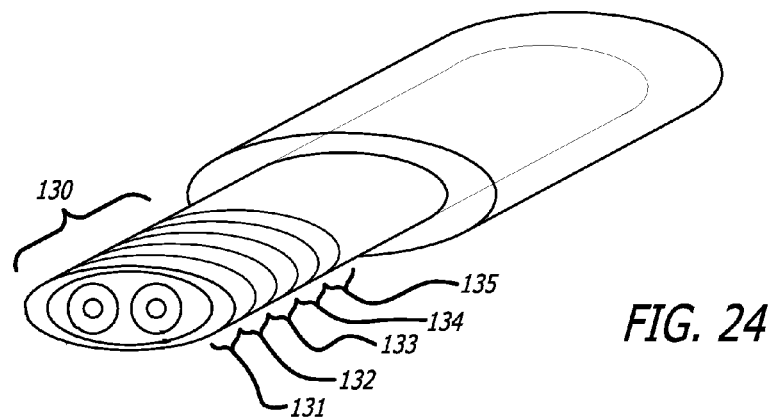
FIG. 24 is an isometric broken away view of a schematic diagram of a guiding catheter in accordance with the present invention in which the guiding catheter has a segmented progressively compliant tip design.

Additionally, any of the embodiments may include a segmented progressively compliant tip design 130 (FIG. 24) that incorporates a compliant polymeric material to minimize vessel trauma. For example, according to one embodiment, the segmented progressively compliant tip design 130 may comprises various segments 131, 132, 133, 134, 135 of different materials and/or the segments may be stepped such that the stiffness of the segmented progressively compliant distal tip 130 varies from one segment to the next. The exterior of the catheter is preferably covered with a polymer material 44 to encapsulate the stainless and/or platinum braid/coil construction. The polymer material preferably has a lubricious hydrophilic outer coating.

It will be apparent from the foregoing that while particular forms of the invention have been illustrated and described, various modifications can be made without departing from the spirit and scope of the invention.

We claim:

1. A guiding catheter, comprising:

an elongated wall structure extending along a length of the catheter defining an inner lumen and a first outer lumen, said inner lumen having a substantially oval cross-sectional shape, the elongated wall structure defining the inner lumen including a plurality of torque transmittal guidance walls having a flat cross-sectional surface, said plurality of torque transmittal guidance walls being made of a different material than a remainder of said elongated wall structure, said plurality of torque transmittal guidance walls being substantially flexible in a dimension perpendicular to the flat cross-sectional surface of said plurality of torque transmittal guidance walls but substantially not flexible in a dimension parallel to the flat cross-sectional surface of said plurality of torque transmittal guidance walls, and said first outer lumen substantially having a cross-sectional shape of a portion of a circle, wherein said first outer lumen is disposed to one side of said inner lumen, and said elongated wall structure defines a second outer lumen having a cross-sectional shape of a portion of a circle disposed to another, opposite side of said inner lumen, and wherein said wall structure defining said inner lumen and said inner lumen extend distally beyond said outer lumens; and an elongated stiffener in said first outer lumen, said elongated stiffener being formed of a polymeric material conforming to the shape of said first outer lumen, and said elongated stiffener including a central wire.

2. The guiding catheter of claim 1, wherein said catheter wall structure defining said lumens includes an outer catheter surface having a substantially circular shaped cross-section that tapers inwardly and distally to an outer catheter surface that continues distally having a noncircular shaped cross-section.

3. The guiding catheter of claim 1, wherein said oval cross-sectional shape of said inner lumen is defined by two parallel line segments connected at each end by two curved line segments.

4. The guiding catheter of claim 3, wherein said two curved line segments are symmetric mirror images of each other.

5. The guiding catheter of claim 1, wherein an outer wall of each of said first and second outer lumens varies in stiffness along its length.

6. The guiding catheter of claim 1, wherein a distal portion of said elongated wall structure is segmented and progressively compliant.

7. The guiding catheter of claim 1, wherein said elongated stiffener varies in stiffness along its length.

8. The guiding catheter of claim 1, wherein said elongated stiffener tapers along at least a portion of its length.

9. The guiding catheter of claim 8, wherein said portion of the length of said elongated stiffener has a continuously changing taper angle.

10. The guiding catheter of claim 8, wherein said portion of the length of said elongated stiffener has contiguous tapered segments having different taper angles.

11. The guiding catheter of claim 1, further comprising a balloon disposed along an outside of the elongated wall structure of the guiding catheter, wherein one of the first or second outer lumens is an inflation/deflation lumen for the balloon.

12. The guiding catheter of claim 1, further comprising a metal cage disposed along an outside of the elongated wall structure of the guiding catheter, and control wires housed within one of the first or second outer lumens that expand/collapse the metal cage.

13. The guiding catheter of claim 1, wherein a layer or a segment of the elongated wall structure of the guiding catheter comprises a material that can be activated so that at least one characteristic of the material changes.

14. The guiding catheter of claim 13, wherein the layer or the segment of the elongated wall structure is capable of changing in response to injection of a liquid into one of the first or second outer lumens.

15. The guiding catheter of claim 13, wherein the layer or the segment of the elongated wall structure is capable of changing in response to insertion of an electric heating element into one of the first or second outer lumens.

16. The guiding catheter of claim 1, wherein said elongated stiffener is secured to a noncircular inner surface of said first outer lumen and is free to move throughout the length of the catheter.

* * * * *